United States Patent
Xiao et al.

(10) Patent No.: US 11,564,904 B2
(45) Date of Patent: *Jan. 31, 2023

(54) GINGKO DITERPENE LACTONE COMPOSITION

(71) Applicant: Jiangsu Kanion Pharmaceutical Co., Ltd., Jiangsu (CN)

(72) Inventors: Wei Xiao, Jiangsu (CN); Xiujuan Chang, Jiangsu (CN); Enli Zhou, Jiangsu (CN); Xiaodong Kang, Jiangsu (CN); Yongxiang Wang, Jiangsu (CN); Hanfei Hu, Jiangsu (CN); Yun Wu, Jiangsu (CN); Zhenzhong Wang, Jiangsu (CN); Chenfeng Zhang, Jiangsu (CN)

(73) Assignee: JIANGSU KANION PHARMACEUTICAL CO., LTD., Jiangsu (CN)

( * ) Notice: Subject to any disclaimer, the term of this patent is extended or adjusted under 35 U.S.C. 154(b) by 18 days.

This patent is subject to a terminal disclaimer.

(21) Appl. No.: 16/771,677

(22) PCT Filed: Nov. 13, 2018

(86) PCT No.: PCT/CN2018/115166
§ 371 (c)(1),
(2) Date: Jun. 10, 2020

(87) PCT Pub. No.: WO2019/128498
PCT Pub. Date: Jul. 4, 2019

(65) Prior Publication Data
US 2021/0069148 A1 Mar. 11, 2021

(30) Foreign Application Priority Data
Dec. 29, 2017 (CN) .......................... 201711475578.2

(51) Int. Cl.
| | |
|---|---|
| *A61K 31/365* | (2006.01) |
| *A61P 9/10* | (2006.01) |
| *A61P 25/00* | (2006.01) |
| *A61K 36/16* | (2006.01) |
| *A61K 9/00* | (2006.01) |

(52) U.S. Cl.
CPC ............ *A61K 31/365* (2013.01); *A61K 36/16* (2013.01); *A61P 9/10* (2018.01); *A61P 25/00* (2018.01); *A61K 9/0019* (2013.01)

(58) Field of Classification Search
CPC .. A61K 31/365; A61K 2300/00; A61K 36/16; A61K 9/0019; A61K 47/26; A61P 25/24; A61P 39/06; A61P 9/10
See application file for complete search history.

(56) References Cited

FOREIGN PATENT DOCUMENTS

| | | | | |
|---|---|---|---|---|
| CN | 1424031 A | * | 6/2003 | .......... A61K 31/365 |
| CN | 1424031 A | | 6/2003 | |
| CN | 1424315 A | | 6/2003 | |
| CN | 1476832 A | | 2/2004 | |
| CN | 107898782 A | | 4/2018 | |
| CN | 107929283 A | | 4/2018 | |

OTHER PUBLICATIONS

English Translation of First Search Report dated Dec. 14, 2018 in CN Application No. 201711475578.2.
English Translation of Supplementary Search Report dated Jan. 25, 2019 in CN Application No. 201711475578.2.
Extended European Search Report dated Nov. 24, 2020 in EP Application No. 18897379.6.
Office Action dated May 25, 2021 in JP Application No. 2020536623.
Office Action dated Dec. 24, 2018 in CN Application No. 201711475578.2.
Shao et al., "Pharmacokinetics of ginkgolides A, B and K after single and multiple intravenous infusions and their interactions with midazolam in healthy Chinese male subjects," Eur. J. Clin. Pharmacol., vol. 73, pp. 537-546 (2017).
Wang et al., "Pharmacokinetics and tissue distribution of ginkgolide A, ginkgolide B, and ginkgolide K after intravenous infusion of ginkgo diterpene lactones in a rat model," Journal of Pharmaceutical and Biomedical Analysis, vol. 126, pp. 109-116 (2016).
Wang et al., "Pharmacokinetics of the prototype and hydrolyzed carboxylic forms of ginkgolides A, B, and K administered as a ginkgo diterpene lactones meglumine injection in beagle dogs," Chinese Journal of Natural Medicines, vol. 15, No. 10, pp. 0775-0784 (2017).
Zhou et al., "Evaluation of in vitro inhibition and induction of cytochrome P450 activities by hydrolyzed ginkogolides," Journal of Ethnopharmacology, vol. 158, pp. 132-139 (2014).
Zhou et al., "Ginkgolides and bilobalide protect BV2 microglia cells against OGD/reoxygenation injury by inhibiting TLR2/4 signaling pathways," Cell Stress and Chaperones, vol. 21, pp. 1037-1053 (2016).
Int'l Search Report dated Feb. 13, 2019 in Int'l Application No. PCT/CN2018/115166.

* cited by examiner

*Primary Examiner* — Jean P Cornet
(74) *Attorney, Agent, or Firm* — Panitch Schwarze Belisario & Nadel LLP

(57) ABSTRACT

A *Ginkgo* diterpene lactone composition is provided. The extract can lower the neurological function score of a cerebral ischemia-reperfusion rat, reduce the cerebral ischemia area and the water content after brain tissue edema, improve SOD activity, and decrease the MDA content. The composition can inhibit rabbit platelet aggregation induced by PAF and ADP inducers at different time points so as to reduce the maximum aggregation rate. In addition, experiments show that the effect of each monomer compound in the *Ginkgo* diterpene lactone composition is significantly increased at certain proportion.

7 Claims, No Drawings

GINGKO DITERPENE LACTONE COMPOSITION

CROSS-REFERENCE TO RELATED APPLICATIONS

This application is a Section 371 of International Application No. PCT/CN2018/115166, filed Nov. 13, 2018, which was published in the Chinese language on Jul. 4, 2019, under International Publication No. WO 2019/128498 A1, which claims priority under 35 U.S.C. § 119(b) to Chinese Application No. 201711475578.2, filed Dec. 29, 2017, the disclosures of each of which are incorporated herein by reference in their entireties.

TECHNICAL FIELD

The present invention belongs to the technical field of medicine and in particular to a fixed-component *Ginkgo* diterpene lactone composition and its application.

BACKGROUND

*Ginkgo biloba* leaves have a wide range of biological activities and contains a variety of chemical components, mainly including flavonoids, terpenes, polysaccharides, phenols, organic acids, alkaloids, amino acids, steroids and trace elements. Among them, the contents of vitamin C, vitamin E, carotene and mineral elements (such as calcium, phosphorus, boron and selenium) are also very high. The most important medicinal components of the *Ginkgo biloba* leaves are flavonoids and terpenes. Flavonoids and terpenes have many functions such as angiectatic and antioxidant effects.

Ginkgolides, as one of the main active ingredients in *Ginkgo biloba* leaves, are a rare class of natural compounds that have not been found in other plants so far. They have antioxidant, anti-inflammatory, anti-platelet aggregation, antiapoptosis, ant-cell death and angiectatic pharmacological effects and also can protect the central nervous system and ischemic tissue. Ginkgolides have strong specific inhibitory activity on receptors and are specific platelet activating factor (PAF) antagonists. They can inhibit PAF-induced platelet aggregation and thromboxane increase in healthy people. Its antagonistic activity is closely related to its chemical structure. PAF is a soluble phospholipid that can cause platelet aggregation and it is also one of the strongest lipid mediators found so far. It plays a key role in a variety of pathological and physiological processes. PAF takes its biological function mainly through a PAF receptor, and PAF receptor antagonists mainly antagonize the biological effects of the PAF receptor by inhibiting the PAF receptor. *Ginkgo* diterpene lactones are currently considered as the natural PAF receptor antagonists with the best clinical application prospects. *Ginkgo* diterpene lactones mainly comprise ginkgolide A (GA), ginkgolide B (GB), ginkgolide C (GC), ginkgolide L (GL), and ginkgolide M (GM), Ginkgolide J (GJ), and Ginkgolide K (GK) which belong to the diterpene lactones, and bilobalides which belong to sesquiterpenes, among which GB has a strong antagonistic effect on PAF. GK is a new monomer with a structure similar to that of GB.

CN1424031A reports a ginkgolide preparation, containing 30-40% of GA, 50-65% of GB, and 0.5-5% of GK. This patent does not conduct in-depth research on the proportional relationship of the various diterpene lactones.

SUMMARY

Based on the prior art, the present invention conducts a more in-depth study, and obtains the weight percentages of GA, GB, and GK in a better ratio by using an ischemic stroke disease model and evaluation indicators such as inhibition of platelet aggregation. Based on this, the inventors have surprisingly found that the *Ginkgo* diterpene lactone composition has a better anti-stroke effect when the ratio of GB to GK is within a certain range.

The present invention relates to a *Ginkgo* diterpene lactone composition, comprising, by weight: 32-36% of GA, 55-60% of GB, and 2.2-3.6% of GK, and the weight ratio of the GB to the GK is 18-22:1.

Preferably, the *Ginkgo* diterpene lactone composition, comprises, by weight: 33.5-35.2% of GA, 56.1-60.1% of GB, and 2.6-3.0% of GK, and the weight ratio of the GB to the GK is 20.0-21.5:1.

Preferably, the content of the GA is 32-34%, and/or the content of the GB is 56-58%, and/or the content of the GK is 2.4-3.4%.

Preferably, the ratio of the GB to the GK is 19-21:1, and more preferably 20:1.

Preferably, the composition may be in the form of an extract or a mixture of *Ginkgo* diterpene lactone monomers;

The present invention also provides a *Ginkgo* diterpene lactone preparation containing the above composition (including the extract), wherein the preparation further comprises pharmaceutically acceptable excipients.

Further, the preparation is a *Ginkgo* diterpene lactone injection.

Specifically, the injection in a dose of 1 ml or 5 ml or 10 ml contains 5±0.5 mg or 25±0.5 mg or 50±0.5 mg of the *Ginkgo* diterpene lactone composition respectively.

Further, the injection further contains meglumine and sodium chloride, and the weight ratio of the *Ginkgo* diterpene lactone composition to meglumine to sodium chloride is (2-8):(2-8):(4-12).

The present invention further provides an application of the above composition in the preparation of a drug for preventing and treating stroke.

The present invention further provides an application of the above composition in the preparation of a drug for inhibiting platelet aggregation.

The present invention further provides an application of the above composition in the preparation of a neuroprotective drug.

The wording "application" refers to administering the above-mentioned composition (including the extract) to a subject having a corresponding disease or a pre-disposition to the disease, with the purpose of conferring a therapeutic effect, such as curing, alleviating, changing, influencing, improving or preventing the disease, its symptoms or its pre-disposition. Those skilled in the art can easily determine the specific effective dose according to the type of disease to be treated, the route of administration and the use of excipients and the dose may vary due to the concurrent use of other drugs.

According to the present invention, a focal cerebral ischemia-reperfusion injury experiment was performed on rats. It was found that the *Ginkgo* diterpene lactone composition can reduce the neurologic scores in rats with cerebral ischemia reperfusion, reduce the area of cerebral ischemia, reduce the brain water content (BWC) after brain edema, improve SOD activity and reduce the MDA content and it was further found that the effect was significantly improved when the *Ginkgo* diterpene lactone monomers are at a certain ratio. The present invention also confirmed that the *Ginkgo* diterpene lactone composition can inhibit platelet aggregation in rabbits induced by PAF and ADP inducers at different time points, and reduce the maximum aggregation rate. Similarly, a better anti-thrombotic effect is achieved when the *Ginkgo* diterpene lactone monomers are at a certain ratio.

DETAILED DESCRIPTION OF EMBODIMENTS

As mentioned above, the present invention is intended to provide a *Ginkgo* diterpene lactone composition. The specific description will be made below in conjunction with the contents of the embodiments.

In particular, it should be noted that similar substitutions and modifications made to the present invention will be apparent to those skilled in the art and they are all considered to be included in the present invention. It is obvious that relevant persons can make modifications or appropriate changes and combinations to the methods and applications described herein without departing from the content, spirit and scope of the present invention to implement and apply the technology of the present invention. Obviously, the described embodiments are only a part of, not all the embodiments of the present invention.

It should be noted that if the specific conditions are not specified, they are performed according to the conventional conditions or the conditions recommended by the manufacturer. If the manufacturers of the APIs or excipients used, and of the reagents or instruments used are not specified, they are all regular products which can be commercially available. Unless stated otherwise, all percentages, ratios, proportions or parts are by weight.

Unless otherwise defined, all technical terms and scientific wording used herein have the same meaning as those familiar to those skilled in the art. In addition, any methods and materials similar or equal to the content described can be applied to the present invention.

Example 1 Protective Effects of the *Ginkgo* Diterpene Lactone Composition on a Cerebral Ischemic Disease Model 1. Materials 1.1 The *Ginkgo* diterpene lactone composition can be prepared by the following method: performing ethanol extraction on *Ginkgo biloba* leaves, concentrating, removing impurities with an adsorbent, eluting with an organic solvent, washing and purifying, and recrystallizing, etc.; and adjusting extraction parameters, adsorbent selection, eluent selection, washing solution selection, and recrystallization solvent selection, to obtain the desired product. Alternatively, the *Ginkgo* diterpene lactone composition can also be prepared by a method disclosed by CN1424031A and by adjusting preparation parameters; and the composition also can be obtained by mixing the compounds. In the above manner, a *Ginkgo* diterpene lactone composition with a ratio as shown in Table 1 was obtained.

Compositions or extracts with different weight percentages were obtained according to the above methods, and the percentage contents of GA, GB and GK were determined as follows:

TABLE 1

The ratio of components in the gingko diterpene lactone composition

| Group | GA | GB | GK | GB/GK |
|---|---|---|---|---|
| Example 1 | 34.1 | 57.4 | 2.8 | 20.5 |
| Example 2 | 33.5 | 56.1 | 2.6 | 21.6 |
| Example 3 | 35.7 | 60.1 | 3.0 | 20.0 |
| Comparison example 1 | 30.7 | 59.5 | 3.2 | 18.6 |
| Comparison example 2 | 39.5 | 56.3 | 2.8 | 20.1 |
| Comparison example 3 | 32.6 | 63.5 | 3.1 | 20.5 |
| Comparison example 4 | 35.4 | 53.4 | 3.2 | 16.7 |
| Comparison example 5 | 36.1 | 59.3 | 1.9 | 31.2 |
| Comparison example 6 | 33.9 | 56.2 | 4.6 | 12.2 |
| Comparison example 7 | 35.6 | 58.4 | 2.1 | 27.8 |
| Comparison example 8 | 32.2 | 53.7 | 3.3 | 16.3 |

Nimodipine, produced by Shandong Xinhua Pharmaceutical Co., Ltd., with a batch number 1609215; 2,3,5-triphenyltetrazolium chloride, produced by Sigma company; superoxide dismutase (SOD) and malondialdehyde (MDA) kits, purchased from Nanjing Jiancheng Bioegineering Research Institute.

1.2 Animals 150 clean-grade male SD rats, weighing 220-250 g, provided by SIPPR/BK Laboratory Animals (Shanghai, China), with a certificate number of SCXK (Shanghai) 2013-0016.

1.3 Instruments

TSQ-280 constant shaking incubator (Shanghai Jinghong Laboratory Instrument Co., Ltd.), 5804R refrigerated centrifuge (Eppendorf Company), BD224S electronic balance (Sartorius Scientific Instruments (Beijing) Co., Ltd.).

2. Methods 2.1 Grouping and Modeling

Rats with qualified weight were randomly assigned to 14 groups: sham-operation group, the model group, the nimodipine group (10.8 mg/kg), and the *Ginkgo* diterpene lactone composition groups (see Table 1) subjected to administration through intravenous injection in a dose of 2.4 g·kg$^{-1}$. All animals were given the corresponding drugs by tail vein injections 1 day before the modeling and 30 min after reperfusion (the sham-operation group and the model group were injected with the same volume of normal saline at the same time point).

According to the method of *Zea longa*. et al., a right middle cerebral artery occlusion (MCAO) model was established by intraluminal suture occlusion in internal carotid artery in rats. Main steps: rats were anesthetized with 10% chloral hydrate (350 mg·kg$^{-1}$) by intra-peritoneal injections. The right external carotid artery was separated, ligated and cut off. The tip-rounded nylon suture was slowly placed 18 mm from the external carotid artery stump along the common carotid artery and the internal carotid artery to block the origin of the middle cerebral artery and cause ischemia. Re-perfusion was performed 3 hours after ischemia and the rats were decapitated to collect brains 24 hours after the re-perfusion. In the sham-operation group, only the common carotid artery, external carotid artery and internal carotid artery were separated but no suture was inserted.

2.2 Detection Indicators 2.2.1 Neurologic score. Referring to the score standard of Longa, after surgery, score 1-2 is a sign of successful surgery; score 0: no obvious neurological symptoms; score 1: inability to fully extend the left forelimb; score 2: rotation to the left; score 3: tipping to the left while walking; score 4: inability to walk on their own.

2.2.2 BWC. Rats were decapitated to collect brains 24 hours after re-perfusion, the wet weight and dry weight (after drying at 100° C. for 48 hours to constant weight) in an electric thermostatic drying oven were measured respectively, to calculate the BWC. BWC (%)=(wet weight-dry weight)/wet weight×100%.

2.2.3 Measurement of infarct size. The rats were decapitated to collect brains 24 hours after re-perfusion. The brains were coronally cut consecutive 2 mm into 5 sections. The brain sections were incubated at 37° C. for 30 minutes in 2% TTC phosphate buffer solution. Normal brain tissue was stained red, and the infarcts were white. The surface liquid was removed with filter paper and pictures taken with a digital camera. The ischemic areas on both sides of each section were calculated with software and the mean ischemic areas were taken.

2.2.4 Detection of serum vitality and MDA content. Blood was taken to separate the serum 24 hours after reperfusion, and the measurement of OD value and the calculation of the SOD and MDA content were conducted according to the instructions.

after ischemia-reperfusion, and significantly reduce the infarct size (P<0.05, P<0.01). The results showed that the *Ginkgo* diterpene lactone composition could reduce neurologic deficit and the cerebral infarction rate of rats, as shown in Table 2.

3.2 BWC

The BWC of rats in the model group was increased significantly and obviously different from that of the sham-operation group (p<0.01) and the nimodipine group and *Ginkgo* diterpene lactone composition groups had significant differences with the model group (P<0.05, P<0.01), indicating that the *Ginkgo* diterpene lactone composition can significantly reduce the BWC after brain edema, as shown Table 2.

3.3 Infarct Size

Compared with the sham-operation group, the model group had the MDA content increased (p<0.01), and the SOD activity decreased (p<0.01). Compared with the model group, the rats in the nimodipine group had the SOD activity enhanced and the MDA content significantly reduced, with a significant difference (p<0.01), and the rats in the *Ginkgo* diterpene lactone composition groups had the SOD activity significantly increased (P<0.05, P<0.01) and the MDA content significantly reduced (P<0.05, P<0.01), as shown in Table 2.

TABLE 2

Effect of the gingko diterpene lactone composition on Neurologic score, brain water content (BWC), SOD activity, and MDA content ($\bar{x} \pm s$, n = 10)

| Group | Neurologic score | BWC % | Infarct size % | SOD/ $U*mg^{-1}$ | MDA/ $nmol* mg^{-1}$ |
|---|---|---|---|---|---|
| Sham-operation | 0 | 59.29 ± 6.60 | 0 | 30.73 ± 4.17 | 5.68 ± 1.13 |
| Model | 3.70 ± 0.48** | 84.61 ± 9.63** | 23.14 ± 4.84** | 21.46 ± 4.05** | 8.13 ± 1.57** |
| Nimodipine | 2.70 ± 0.95 | 68.36 ± 8.97 | 15.49 ± 5.94 | 26.94 ± 4.37 | 5.79 ± 1.75 |
| Example 1 | 2.00 ± 0.82 | 61.99 ± 14.90 | 13.27 ± 4.63 | 30.25 ± 5.17 | 5.02 ± 1.36 |
| Example 2 | 2.70 ± 0.82 | 69.88 ± 9.89 | 15.37 ± 5.58 | 28.29 ± 3.79 | 6.10 ± 1.42 |
| Example 3 | 2.70 ± 0.95 | 72.04 ± 4.73 | 16.00 ± 4.72 | 28.12 ± 4.54 | 5.96 ± 1.36 |
| Comparison example 1 | 2.90 ± 0.74▲ | 74.51 ± 11.27▲ | 17.96 ± 4.60▲ | 25.55 ± 4.63▲ | 6.53 ± 1.43▲ |
| Comparison example 2 | 2.90 ± 0.99▲ | 74.39 ± 10.29▲ | 18.12 ± 5.42▲ | 23.7 ± 3.19▲▲ | 6.53 ± 1.81▲ |
| Comparison example 3 | 2.80 ± 0.79▲ | 74.34 ± 10.85▲ | 18.12 ± 4.49▲ | 25.40 ± 4.03▲ | 6.59 ± 1.15▲ |
| Comparison example 4 | 2.90 ± 0.88▲ | 74.42 ± 10.87▲ | 17.64 ± 3.83▲ | 25.73 ± 4.36▲ | 6.46 ± 1.62▲ |
| Comparison example 5 | 3.00 ± 0.82▲ | 74.31 ± 10.79▲ | 18.80 ± 4.37▲ | 25.42 ± 4.31▲ | 6.53 ± 1.47▲ |
| Comparison example 6 | 2.90 ± 0.99▲ | 75.21 ± 8.46▲ | 18.78 ± 3.38▲▲ | 25.17 ± 3.44▲ | 6.52 ± 1.55▲ |
| Comparison example 7 | 2.90 ± 0.99▲ | 74.73 ± 8.74▲ | 20.02 ± 6.81▲ | 25.46 ± 4.14▲ | 6.41 ± 1.50▲ |
| Comparison example 8 | 3.00 ± 0.67▲▲ | 74.46 ± 9.15▲ | 18.30 ± 5.23▲ | 25.74 ± 4.34▲ | 6.50 ± 1.55▲ |

Compared with sham-operation group: *p < 0.05, **p < 0.01; compared with Example 1: ▲p < 0.05, ▲▲p < 0.01.

2.3 Statistical Processing

The experimental data was expressed as $\bar{x} \pm s$ and analyzed by SPSS 17.0 statistical software. The comparison of means between multiple groups was performed by one-way analysis of variance. The comparison of sample means between two groups was performed by q test. P<0.05 was considered statistically significant.

3. Results 3.1 Neurologic Score

After cerebral ischemia-reperfusion, compared with the model group, both the *Ginkgo* diterpene lactone composition groups and the nimodipine group can significantly reduce the neurologic score of the rats (P<0.05, P<0.01), and significantly improve the behavioral disorders of the rats 4 Conclusion It can be seen from Table 2 that there is no significant difference between the groups of Examples 2-3 and the groups of Example 1, the groups of Example 1 have a significant difference as compared with the groups of Comparison Examples 1-8.

In the *Ginkgo* diterpene lactone compositions of Examples 1-3, the content of GA is in the range of 32-36%, the content of GB is in the range of 55-60%, and the content of GK is 2.2-3.6%, and the weight ratio of GB to GK is in the range of 18-22:1. Compared with the *Ginkgo* diterpene lactone composition in Comparison Examples 1-8, the *Ginkgo* diterpene lactone compositions of Examples 1-3 achieve good effects for the rats after the cerebral ischemiare-perfusion in the reduction of the neurologic score, reduction of the area of cerebral ischemia, reduction of BWC after edema, increase of SOD activity, reduction of MDA content, and have a better protective effect on the focal cerebral ischemia-reperfusion injury in rats, that is, it has better protective effect on focal cerebral ischemia-re-perfusion injury in rats.

The present invention also provides a method for preparing an extract with a relatively stable component ratio. Specifically, 50 kg of a medicinal material of *Ginkgo biloba* leaves (dried leaves of *Ginkgo biloba Ginkgo biloba* L., purchased from Pizhou, Jiangsu) were added with 8-fold 10% ethanol, heated for reflux extraction twice, each time for 1.5 hours. The extracting solutions were combined, concentrated and filtered to obtain a concentrated solution. Polyamide in an weight amount 15% of *Ginkgo biloba* leaves was added to the concentrated solution and stirred 36 hours for adsorption, the solution was rested overnight, the supernatant was removed and the adsorbent was collected. 30 L of 95% ethanol was added to the adsorbent, then heated to boiling for 1.5 hours; the solution was then cooled naturally; the supernatant is collected; 30 L of ethanol was added to the absorbent after extraction and the extraction was repeated 3 times; the extracting solutions obtained from the above four times of extraction were combined and concentrated under reduced pressure to obtain a concentrated solution ($d=1.40$); and the concentrated solution was refrigerated for 5 days. The refrigerated concentrated solution was centrifuged, the precipitate was collected and washed with water for 3 times; the water solution was removed and then the precipitate was reflux extracted three times with 2-fold ethanol, each time for 1 hour; the extracting solution was filtered and collected, and the solvent was recovered to dryness, thus obtaining crude total lactone of *Ginkgo*. The crude total lactone of *Ginkgo* was washed three times with 1-fold (weight ratio) water, the water solution was then removed, and the precipitate was repeatedly recrystallized from three times with 3-fold (weight ratio) ethanol and then dried to obtain the raw *Ginkgo* diterpene lactone. After testing, in the raw *Ginkgo* diterpene lactone, the content of GA was 35%, the content of GB was 58%, and the content of GK was 3.1%.

The above steps were repeated three times. The SDs of the contents of GA, GB, and GK are small, all within 5%.

Example 2 Protective Effect of the *Ginkgo* Diterpene Lactone Composition on Platelet Aggregation in Rabbits 1. Experimental Materials
1.1 Instruments
STEELIEX platelet aggregation coagulation factor analyzer, provided by Beijing Shidi Scientific Instrument Co., Ltd.; LDZ5-2 centrifuge, provided by Beijing Medical Centrifuge Factory.
1.2 Reagents and Drugs
The specific proportions of the drug groups were the same as in Table 1.
Nimodipine, produced by Shandong Xinhua Pharmaceutical Co., Ltd., with a batch number 1609215; adenosine diphosphate (ADP), provided by Shanghai Boao Biotechnology Co., Ltd. (imported and repacked); platelet activating factor (PAF), provided by Sigma Company; and Trisodium citrate, provided by Shanghai Lingfeng Chemical Reagent Co., Ltd.

1.3 Experimental Animals
New Zealand white rabbits, provided by Laifu Breeding Farm in Pukou District, Nanjing City, with the experimental animal production license SCXK (Jiangsu) 2014-0004, and the animal license SYXK (Jiangsu) 2013-0021.

2. Experimental Methods
Determination of In Vitro Platelet Aggregation Rate of Rabbits
Rabbits were treated with procaine by local anesthesia, carotid arterial cannulation and bleeding. The blood was subjected to anti-coagulation by using a 3.8% sodium citrate solution and centrifuged at 1000 r/min for 10 min to collect platelet-rich plasma (PRP), and the remaining was centrifuged at 3000 r/min to collect platelet-poor plasma (PPP). The used aggregation inducers were ADP (with the final concentration of 5.4 µg/ml) and PAF (with the final concentration of 0.37 µg/ml), respectively. 250 µl of PRP in each tube was, respectively, added with 10 µl of each *Ginkgo* diterpene lactone composition (with the final concentration of 9.26 µg/ml) and 10 µl of nimodipine (with the final concentration of 0.05 µg/ml), and the PRP control group was added with 10 µl of normal saline. Incubation was performed for 5 min, then 10 µl of 146 µg/ml ADP and 10 µl of 10 µg/ml PAF were added in turn. The platelet aggregation rate and maximum aggregation rate induced by the two inducers at 1 min and 5 min were detected respectively, and the platelet aggregation inhibition rates were calculated according to the equation.

Aggregation inhibition rate (%)=(maximum aggregation rate of blank control group−maximum aggregation rate of administration group)/maximum aggregation rate of blank control group× 100%.

2.2 Statistical Processing
The experimental data was expressed as $\bar{x} \pm s$ and analyzed by SPSS 17.0 statistical software. The comparison of means between multiple groups was performed by one-way analysis of variance. The comparison of sample means between two groups was performed by q test. $P<0.05$ was considered statistically significant.

3. Results
3.1 Effect of In Vitro Application of the *Ginkgo* Diterpene Lactone Composition on Platelet Aggregation Rate of PAF Induced Rabbits
The results showed that the *Ginkgo* diterpene lactone combination externally applied at the finally concentration of 9.26 µg/ml significantly inhibited the maximum platelet aggregation rates of rabbits induced by PAF and significantly inhibited the aggregation rate of platelets at 1 min and 5 min, and showed a significant difference as compared with the blank control group ($p<0.01$, $P<0.05$). For the results, see Table 3.

TABLE 3

Effect of the gingko diterpene lactone composition on PAF-induced platelet aggregation rate of rabbits ($\bar{x} \pm s$, n = 10)

| Group | Platelet aggregation rate | | | Inhibition rate (%) |
|---|---|---|---|---|
| | 1 min | 5 min | Max | |
| Control group | 32.47 ± 4.84 | 56.83 ± 6.44 | 65.88 ± 9.73 | — |
| Nimodipine | 27.13 ± 2.06** | 42.18 ± 9.73** | 48.08 ± 5.82** | 27.02 |
| Example 1 | 24.75 ± 3.48** | 42.89 ± 6.99** | 50.42 ± 5.14** | 23.47 |
| Example 2 | 26.63 ± 3.31** | 43.03 ± 9.48** | 52.85 ± 5.43** | 19.77 |
| Example 3 | 26.97 ± 3.08** | 43.43 ± 7.89** | 52.10 ± 5.50** | 20.90 |

TABLE 3-continued

Effect of the gingko diterpene lactone composition on
PAF-induced platelet aggregation rate of rabbits ($\bar{x} \pm s$, n = 10)

| Group | Platelet aggregation rate | | | Inhibition rate (%) |
|---|---|---|---|---|
| | 1 min | 5 min | Max | |
| Comparison example 1 | 27.92 ± 2.85*▲ | 49.83 ± 5.36*▲ | 57.36 ± 6.35*▲ | 12.92 |
| Comparison example 2 | 28.13 ± 2.74*▲ | 49.64 ± 7.25*▲ | 55.96 ± 5.51*▲ | 15.06 |
| Comparison example 3 | 28.24 ± 3.90*▲ | 50.15 ± 7.00*▲ | 57.00 ± 7.39*▲ | 13.48 |
| Comparison example 4 | 28.24 ± 2.75*▲ | 49.95 ± 7.03*▲ | 56.85 ± 6.79*▲ | 13.70 |
| Comparison example 5 | 28.20 ± 2.88*▲ | 49.98 ± 8.04*▲ | 56.79 ± 5.97*▲ | 13.79 |
| Comparison example 6 | 28.39 ± 2.53*▲ | 50.17 ± 6.93*▲ | 56.43 ± 6.32*▲ | 14.34 |
| Comparison example 7 | 27.74 ± 2.39*▲ | 49.43 ± 6.88*▲ | 56.46 ± 4.49*▲ | 14.29 |
| Comparison example 8 | 28.21 ± 2.94*▲ | 50.12 ± 7.46*▲ | 56.92 ± 6.14*▲ | 13.60 |

Compared with control: **$p < 0.01$, *$p < 0.05$; compared with Example 1: ▲$p < 0.05$, ▲▲$p < 0.01$ 3.2 Effect of In Vitro Application of the *Ginkgo* Diterpene Lactone Composition on Platelet Aggregation Rate of ADP-Induced Rabbits The results showed that the *Ginkgo* diterpene lactone combination externally applied at the finally concentration of 9.26 μg/ml had a certain inhibitory effect on ADP-induced platelet aggregation rates of rabbits at 1 min and 5 min, and showed a significant difference as compared with the blank control group ($p < 0.05$, 0.01). For the results, see Table 4.

TABLE 4

Effect of the gingko diterpene lactone composition on
ADP-induced platelet aggregation rate of rabbits ($\bar{x} \pm s$, n = 10)

| Group | Platelet aggregation rate | | | Inhibition rate (%) |
|---|---|---|---|---|
| | 1 min | 5 min | Max | |
| Control group | 35.06 ± 5.67 | 47.48 ± 6.26 | 49.82 ± 6.75 | — |
| Nimodipine | 26.46 ± 4.41** | 38.33 ± 5.80** | 41.85 ± 4.87** | 16.00 |
| Example 1 | 26.42 ± 2.71** | 36.57 ± 3.48** | 39.16 ± 3.72** | 21.40 |
| Example 2 | 27.28 ± 3.53** | 38.43 ± 5.36** | 40.47 ± 4.93** | 18.77 |
| Example 3 | 27.29 ± 3.82** | 37.91 ± 4.62** | 41.61 ± 4.44** | 16.49 |
| Comparison example 1 | 30.15 ± 4.24*▲ | 41.74 ± 5.52*▲ | 43.84 ± 5.93*▲ | 12.00 |
| Comparison example 2 | 29.97 ± 3.61*▲ | 42.15 ± 4.91*▲▲ | 42.88 ± 3.63*▲ | 13.94 |
| Comparison example 3 | 29.83 ± 3.96*▲ | 40.97 ± 4.61*▲ | 43.02 ± 3.91**▲ | 13.65 |
| Comparison example 4 | 29.91 ± 3.62*▲ | 41.50 ± 5.66*▲ | 43.27 ± 4.65*▲ | 13.15 |
| Comparison example 5 | 30.26 ± 3.45*▲ | 40.36 ± 4.42*▲ | 43.41 ± 2.93*▲ | 12.86 |
| Comparison example 6 | 30.07 ± 3.68*▲ | 41.70 ± 4.89*▲ | 43.84 ± 5.44*▲ | 12.00 |
| Comparison example 7 | 29.93 ± 4.15*▲ | 40.59 ± 4.38*▲ | 43.49 ± 5.12*▲ | 12.70 |
| Comparison example 8 | 29.88 ± 3.53*▲ | 40.89 ± 4.54*▲ | 43.50 ± 4.57*▲ | 12.68 |

Compared with control: **$p < 0.01$, *$p < 0.05$; compared with Example 1: ▲$p < 0.05$, ▲▲$p < 0.01$ 4 Conclusion It can be seen from Table 3 that there is no significant difference between the groups of Examples 2-3 and the group of Example 1, that is, the group of Example 1 have a significant difference as compared with the groups of Comparison Examples 1-8.

In the *Ginkgo* diterpene lactone compositions of Examples 1-3, the content of GA is in the range of 32-36%, the content of GB is in the range of 55-60%, and the content of GK is 2.2-3.6%, and the weight ratio of GB to GK is in the range of 18-22:1. Compared with the *Ginkgo* diterpene lactone compositions of Comparison Examples 1-8, the *Ginkgo* diterpene lactone compositions of Example 1-3 achieve better effects in inhibiting the platelet aggregation of rabbits induced by PAF and ADP at different time points and reducing the maximum aggregation rate. This indicates that the *Ginkgo* diterpene lactone compositions of Example 1-3 have a better antithrombotic effect which is closely related to their efficient and extensive inhibition of platelet aggregation.

The above are only the preferred embodiments of the present invention. It should be noted that, for those with only ordinary skill in the art, without departing from the principles of the present invention, several improvements and retouches can be made, and these improvements and retouches should also be regarded as falling within the scope of the present invention.

What is claimed is:

1. A *Ginkgo* diterpene lactone composition comprising, by weight: 33.5-35.2% of Ginkgolide A, 56.1-60% of Ginkgolide B, and 2.6-3.0% of Ginkgolide K, wherein the weight ratio of the Ginkgolide B to the Ginkgolide K is 20.0-21.5:1.

2. A *Ginkgo* diterpene lactone injection containing the composition according to claim 1.

3. The injection according to claim 2, wherein the injection is in a dose of 1 ml or 5 ml or 10 ml, containing 5±0.5 mg or 25±0.5 mg or 50±0.5 mg of the *Ginkgo* diterpene lactone composition, respectively.

4. The injection according to claim 2, further containing meglumine and sodium chloride, wherein the weight ratio of the *Ginkgo* diterpene lactone composition to meglumine to sodium chloride is (2-8):(2-8):(4-12).

5. A *Ginkgo* diterpene lactone injection comprising the composition according to claim 1 and pharmaceutically acceptable excipients.

6. A method for treating stroke comprising administering an effective dose of a drug comprising the composition according to claim 1.

7. A method for inhibiting platelet aggregation comprising administering an effective dose of a drug comprising the composition according to claim 1.

* * * * *